(12) United States Patent
Chen (10) Patent No.: US 7,850,307 B2
(45) Date of Patent: Dec. 14, 2010

(54) EYEBALL LOCATING METHOD AND SYSTEM

(75) Inventor: Yu-Chia Chen, Hsinchu (TW)

(73) Assignee: Coretronic Corporation, Hsin-Chu (TW)

( * ) Notice: Subject to any disclaimer, the term of this patent is extended or adjusted under 35 U.S.C. 154(b) by 116 days.

(21) Appl. No.: 12/379,015

(22) Filed: Feb. 11, 2009

(65) Prior Publication Data

US 2009/0225278 A1 Sep. 10, 2009

(30) Foreign Application Priority Data

Mar. 5, 2008 (TW) .............................. 97107593 A (51) Int. Cl.
*A61B 3/14* (2006.01)
*A61B 3/00* (2006.01)

(52) U.S. Cl. ..................... 351/209; 351/208; 351/210; 351/246

(58) Field of Classification Search ................. 351/209, 351/210
See application file for complete search history.

(56) References Cited

U.S. PATENT DOCUMENTS 5,987,151 A * 11/1999 Akashi ....................... 382/100
6,836,751 B2 * 12/2004 Paxton et al.
7,083,280 B2 * 8/2006 Hakamata ................... 351/209
7,091,471 B2 * 8/2006 Wenstrand et al.
2004/0070730 A1 * 4/2004 Mihashi et al. ............. 351/221
2004/0196433 A1 * 10/2004 Durnell
2004/0252277 A1 * 12/2004 Chmielewski, Jr. et al.

FOREIGN PATENT DOCUMENTS

TW 372301 9/1987

\* cited by examiner

*Primary Examiner*—Jordan M. Schwartz
(74) *Attorney, Agent, or Firm*—Bacon & Thomas, PLLC (57) ABSTRACT

An eyeball locating system includes a display panel, an application program and a matrix optical sensor. The matrix optical sensor is disposed in the display panel. The application program controls the matrix optical sensor, executing an eyeball locating method to measure the movement of an eyeball including an eye white and a pupil. The method includes: providing a default graph showing the change of light energy; defining a default characteristic value of the pupil according to the default graph; shining light on the eye white and the pupil, a part of the light reflected by the eye white and the pupil to form a reflecting light; detecting the reflecting light energy to form a measured graph showing the change of reflected light energy; calculating a measured characteristic value according to the measured graph; and comparing the default with the measured characteristic values to determine the change of the pupil.

17 Claims, 7 Drawing Sheets

EYEBALL LOCATING METHOD AND SYSTEM

BACKGROUND OF THE INVENTION (1) Field of the Invention

The present invention relates to an eyeball locating method and system, particularly to an eyeball locating method and system using an optical sensor for determining the light reflected by the surface of the eyeball.

(2) Description of the Prior Art

Computer makes people's daily life more and more convenient, but for most disabled men, it is rather inconvenient to handle computer.

To help the disabled men to handle computer, several control methods of the man-machine interface system have been developed in the world, such as hand joint control, voice control, electromyogram (EMG) behavior, shoulder control, gassing and so on. The common disadvantage among these control methods is that they are not capable of executing complex control behaviors, and they are also unable to control the computer conveniently and real-timely because the control signal needs complex identification and longer processing period.

To conquer these limits, the technology of using the movement of eyeball to control the computer emerges as the times require. The eyeball tracking system is most common, which is capable of controlling the cursor or keyboard of the computer by detecting the movement of the eyeball in real time. At present, the eyeball tracking system has piezoelectric type, optical type and magnetic type according to the detection principles.

The piezoelectric type is detecting the movement direction of the eyeball by the change of eye pressure, which is pasting the piezoelectric sensor around the eyes, converting the eye pressure into electrical signal by the piezoelectric sensor and measuring the electrical signal. However this system influences the measurement of the electrical signal easily due to sweat.

The magnetic type is measuring the movement of the eyes by forming magnetic field around the eyeball.

The optical type is capturing an eyeball image, coordinating the present target position through algorithm of image analysis, sending the results to the personal computer and driving mouse to execute control instruction.

Figure 1:
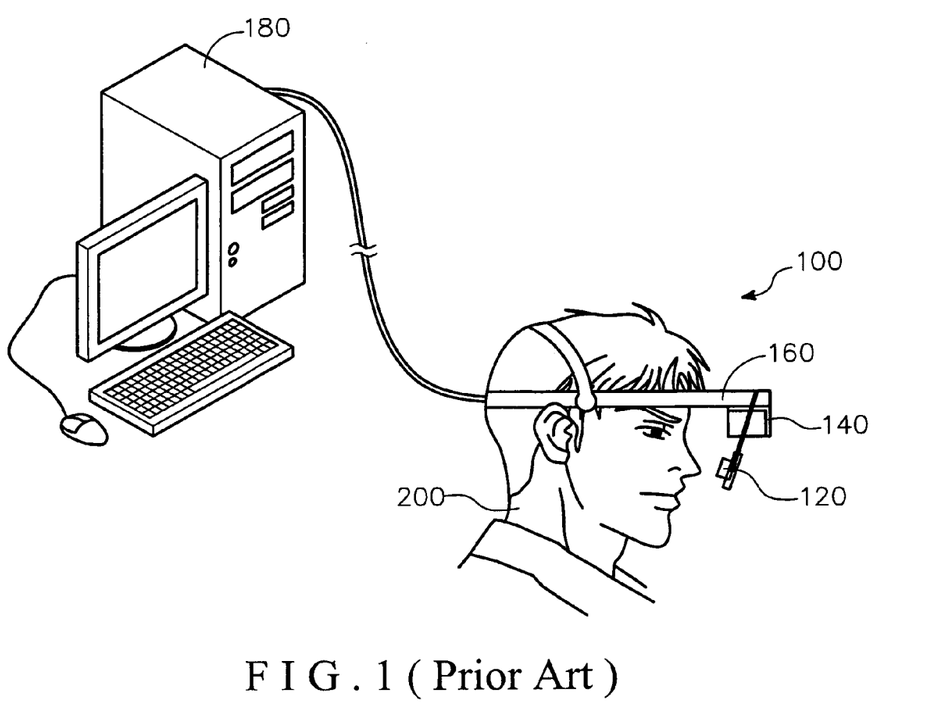
FIG. 1 is a schematic view of the conventional optical eyeball tracking system.

Refer to FIG. 1 for the head-mounted optical eyeball tracking system 100. The eyeball tracking system 100 has a charge-coupled device (CCD) image detector 120, a screen 140 and a frame 160. The CCD image detector 120 is electrically connected to the screen 140 and disposed on the frame 160 together with the screen 140. When an user 200 wears the frame 160, the CCD image detector 120 and the screen 140 are fixed near the eyes of the user 200 by the frame 160. The screen 140 displays a plurality of the location points (not shown) for the user 200. When the user 200 watches one of the location points on the screen 140, the CCD image detector 120 captures his pupil image and performs binary processing to get the position of the pupil.

Furthermore, the CCD image detector 120 is connected to a computer 180. The CCD image detector 120 collects and analyzes the pupil image real-timely, and converts it into a control order to command the cursor to handle the computer 180.

However, the user 200 of the eyeball tracking system 100 needs to wear the frame 160 to increase success rate. The difficulty of the optical detection is when capturing the pupil image, the contrast ratio between the pupil and the eye white is too low to measure, especially under the condition of glasses obstruct, outer light disturb or eyeball pathological changes. In conclusion, the conventional eyeball tracking system 100 is limited in use and has low resolution, which makes it hard to apply in the view or browsing equipments or general medical occasion.

SUMMARY OF THE INVENTION

The present invention is to provide an eyeball locating method and system capable of rising the successful rate of eyeball locating, and being used more conveniently.

For achieving one, some or all of the above mentioned object, an eyeball locating method is provided as an embodiment of the present invention. The eyeball locating method is used to measure the movement of an eyeball including an eye white and a pupil, the method includes the steps of: providing a default graph showing the change of light energy; defining a default characteristic value of the pupil according to the default graph showing the change of light energy; shining light on the eye white and the pupil wherein at least a part of the light is reflected by the eye white and the pupil, so as to form a reflecting light; detecting the energy of the reflecting light, so as to form a measured graph showing the change of reflected light energy; calculating a measured characteristic value according to the measured graph showing the change of reflected light energy; and comparing the default characteristic value with the measured characteristic value to determine the change of the pupil.

In one embodiment, the default characteristic value is the default contrast ratio between the eye white and the pupil, and the measured characteristic value is the measured contrast ratio between the eye white and the pupil.

In one embodiment, the default characteristic value is the default width of the pupil, and the measured characteristic value is the measured width of the pupil.

In above, the step of comparing the default characteristic value with the measured characteristic value to determine the change of the pupil includes determining the width, displacement or area change of the pupil. The step of determining the displacement change of the pupil includes determining a vertical displacement, a horizontal displacement or a near-far displacement of the pupil.

In one embodiment, the eyeball locating method further includes the steps of: providing a matrix optical sensor for shining the light and detecting the energy of the reflected light; measuring the time difference between the light emitted from the matrix optical sensor and the reflecting light coming back to the matrix optical sensor; and calculating the distance between the matrix optical sensor and the eyeball according to the light speed and the time difference.

An eyeball locating system is provided as an embodiment of the present invention. The eyeball locating system includes a display panel, a matrix optical sensor, an application program. The matrix optical sensor is disposed in the display panel, for shining light on the eyeball. Wherein, at least a part of the light is reflected by the eye white and the pupil to form a reflecting light, and the matrix optical sensor detects the energy of the reflecting light. The application program provides a default graph showing the change of light energy to define a default characteristic value of the pupil, and controls the matrix optical sensor, so as to form a measured graph showing the change of reflected light energy according to the energy of the reflecting light. The application program calculates a measured characteristic value according to the measured graph showing the change of reflected light energy and compares the default characteristic value with the measured characteristic value to determine the change of the pupil.

In one embodiment, the matrix optical sensor is selected from the group consisting of a CCD sensor, a CMOS (complementary metal-oxide semiconductor) sensor and an infrared sensor.

In one embodiment, the default or measured characteristic value is the contrast ratio between the eye white and the pupil, or a width, a displacement, an area of the pupil.

In above, both the default graph showing the change of light energy and the measured graph showing the change of reflected light energy show the relationship between the light reflectivity and time.

Accordingly, the embodiments of the present invention compares the default characteristic value with the measure characteristic value based on the default graph showing the change of light energy for determining the change of the pupil more accurately.

Other objectives, features and advantages of the present invention will be further understood from the further technological features disclosed by the embodiments of the present invention wherein there are shown and described preferred embodiments of this invention, simply by way of illustration of modes best suited to carry out the invention.

BRIEF DESCRIPTION OF THE DRAWINGS

The present invention will now be specified with reference to its preferred embodiment illustrated in the drawings, in which.

DESCRIPTION OF THE PREFERRED EMBODIMENTS

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component directly or one or more additional components are between "A" component and "B" component. Also, the description of "A" component "adjacent to" "B" component herein may contain the situations that "A" component is directly "adjacent to" "B" component or one or more additional components are between "A" component and "B" component. Accordingly, the drawings and descriptions will be regarded as illustrative in nature and not as restrictive.

Figure 2:
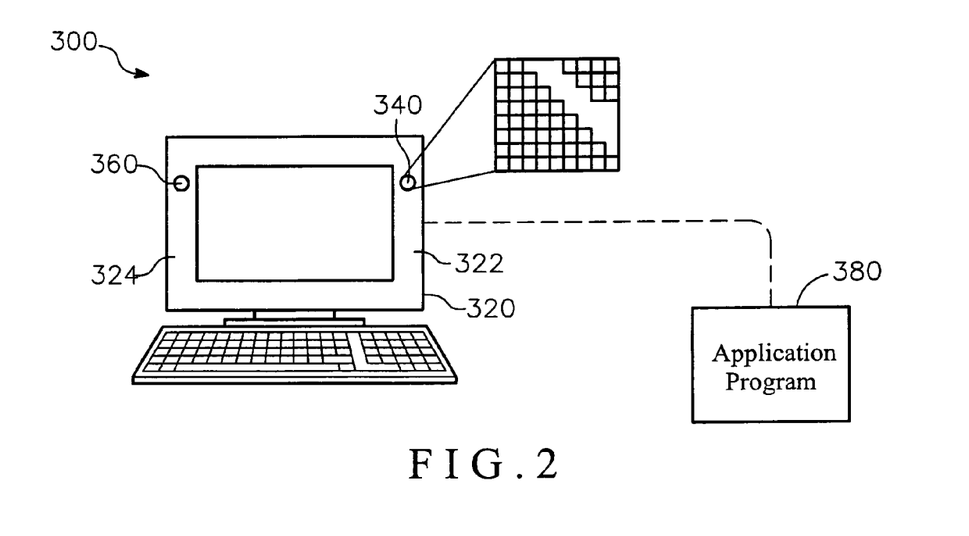
FIG. 2 is a schematic view showing an embodiment of the eyeball locating system according to the present invention.
Figure 3:
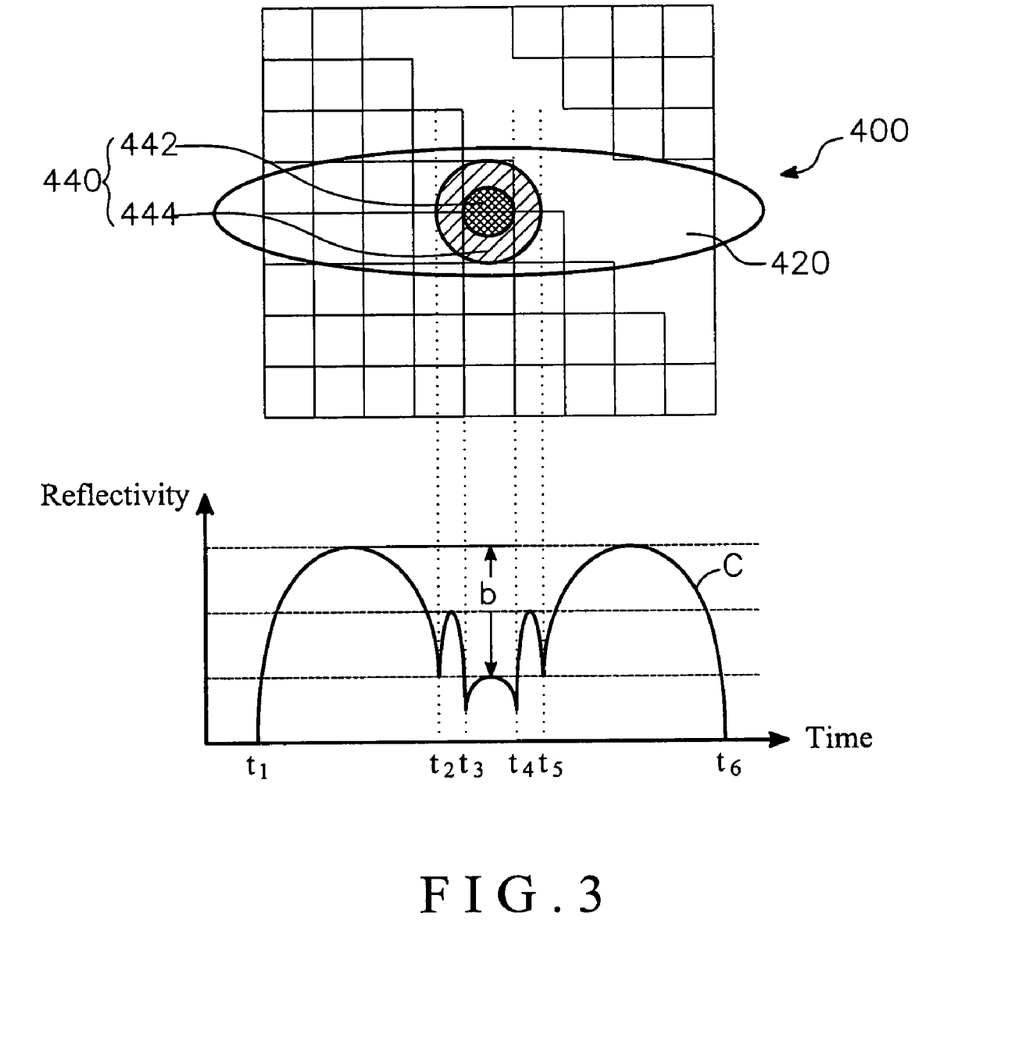
FIG. 3 is a schematic view showing the eyeball structure and the default light energy change graph according to an embodiment of the present invention.

Refer to FIG. 2 for an eyeball locating system 300 to measure the movement of an eyeball 400. The eyeball locating system 300 includes a display panel 320, a first matrix optical sensor 340, a second matrix optical sensor 360 and an application program 380. Referring to FIG. 3, the eyeball 400 has an eye white 420 and a pupil area 440 which has a pupil 442 and an iris 444.

Referring to FIG. 2, the first matrix optical sensor 340 and the second matrix optical sensor 360 are disposed separately at two sides 322 and 324 of the display panel 320. In this embodiment, both the first matrix optical sensor 340 and the second matrix optical sensor 360 are the components providing optical signal emission and induction, shining light on the surface of the eyeball 400 respectively. At least a part of the light is reflected by the eye white 420 and the pupil 442, so as to form a reflecting light. Additionally, the first matrix optical sensor 340 and the second matrix optical sensor 360 each detect the energy of the reflecting light from itself. It should be noted that the first matrix optical sensor 340 and the second matrix optical sensor 360 in this embodiment are used to determine the energy of the reflecting light accurately, but the form or number of the matrix optical sensor is not limited. In other words, applying single matrix optical sensor, or an independent optical emitter with an optical sensor may also achieve the optical signal emission and induction.

The application program 380 provides a default graph showing the change of light energy, which may be used to define a default characteristic value of the pupil 442, such as the default contrast ratio of the eye white 420 and the pupil 442, the width, the area and the displacement of the pupil 442.

In addition, the application program 380 converts the energy of the reflecting light detected by the first matrix optical sensor 340 and the second matrix optical sensor 360 into numerical value by a microprocessor (not shown), so as to form the first and the second graphs showing the change of reflected light energy, and calculates a measured characteristic value of the pupil 442, such as the measured contrast ratio of the eye white 420 and the pupil 442, the width, the area and the displacement of the pupil 442. By comparing the default characteristic value with the measured characteristic value, the application program 380 is able to determine the change of the pupil 442.

Refer to FIG. 3 for the relationship between the default graph C showing the change of light energy and the eye white 420, the iris 444 and the pupil 442. In a preferable embodiment, the longitudinal axis of the graph C is optical reflectivity and the lateral axis is time. As shown in FIG. 3, the curves from the time t1 to t2 and the time t5 to t6 are the default curves showing the optical reflectivity change of the eye white 420. The curve from the time t2 to t5 is the default curve showing the optical reflectivity change of the pupil area 440. The curves from the time t2 to t3 and the time t4 to t5 are the default curves showing the optical reflectivity change of the iris 444. The curve from the time t3 to t4 is the default curve showing the optical reflectivity change of the pupil 442.

As for the definition of the default and measured characteristic values, the example is taken below.

After the contrast ratio of the eye white 420 and the pupil 442 is defined, the areas below the optical reflectivity change curves from the time t1 to t2 and the time t3 to t4 may be calculated separately, and then the ratio of the two areas is obtained. Another method to define the contrast ratio of the eye white 420 and the pupil 442 is comparing the height difference of the peaks of the optical reflectivity change curves from the time t1 to t2 and the time t3 to t4, for example, the height difference b in FIG. 3 represents the contrast ratio of the eye white 420 and the pupil 442.

Each time interval of the graph C showing the change of light energy has a conversion relationship with the width, area or displacement of the pupil 442. For instance, assuming the scanning speed of the first matrix optical sensor 340 or the second matrix optical sensor 360 is constant and the part scanned from t3 to t4 is the pupil 442, the width of the pupil 442 may be calculated by the scanning speed and the time interval t3-t4. Thus, these default characteristic values may be defined according to the graph C showing the change of light energy.

Refer to FIG. 4 to FIG. 7 for the embodiment of the first or second graph showing the change of reflected light energy. The first matrix optical sensor 340 and the second matrix optical sensor 360 are used in practice to measure the eye white 420 and the pupil 442. The reflectivity of the eye white 420 is high, so the signal of the reflecting light from the eye white 420 is strong, while the reflectivity of the pupil 442 is low, so the signal of the reflecting light from the pupil 442 is weak. Accordingly, the first or second graph showing the change of reflected light energy is obtained. By comparing the waves of the graphs C1, C2, C3, C4 showing the change of reflected light energy with the default graph C showing the change of light energy, the eyeball 400 may be located. For convenient comparison with the graph C, all the longitudinal axes of the graphs C1, C2, C3, C4 are optical reflectivity and all the lateral axes are time.

Figure 4:
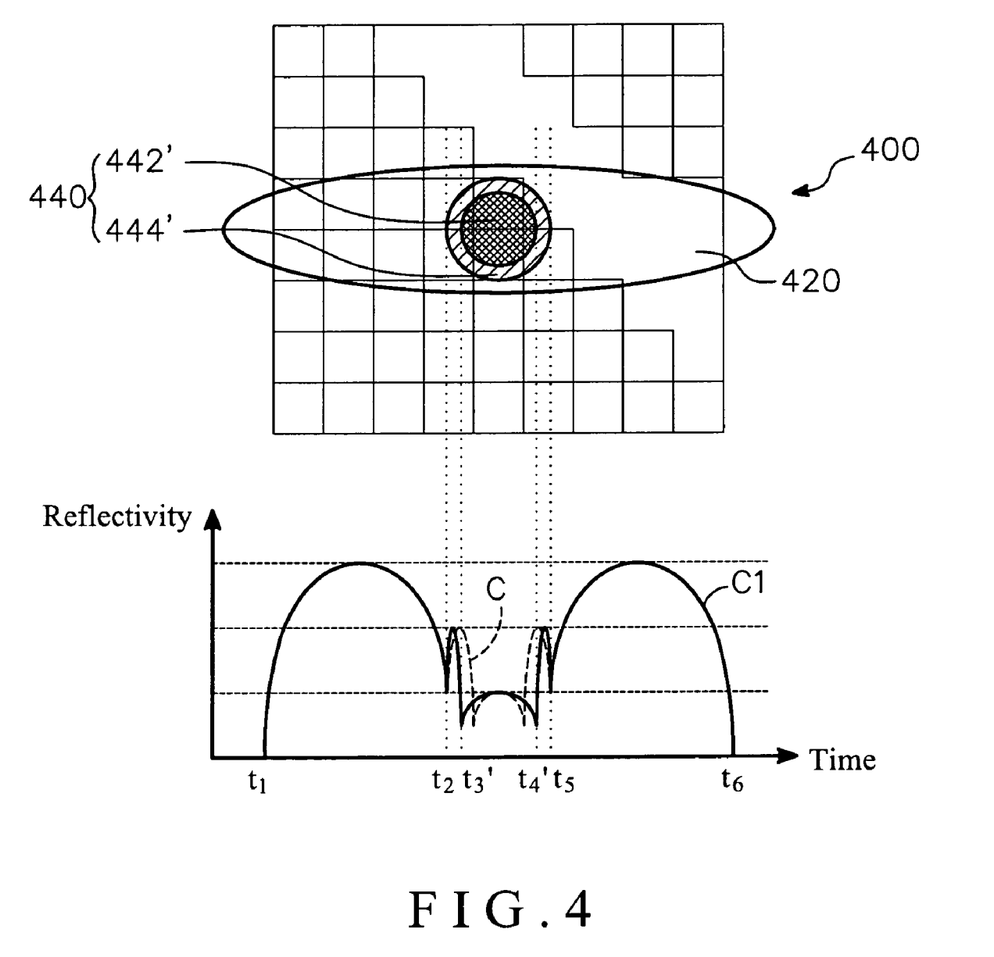
FIG. 4 to FIG. 7 are schematic views showing the eyeball movement and the measured reflected light energy change graph according to an embodiment of the present invention.

Referring to FIG. 4, comparing the default graph C showing the change of light energy (broken line) and the graph C1 showing the change of reflected light energy, it appears that the current time intervals t1-t2 and t5-t6 do not change, but the time intervals t2-t3' and t4'-t5 are shorter than the default time intervals t2-t3 and t4-t5, while the time interval t3'-t4' is longer than the default time interval t3-t4. It represents that at this time the eyeball 400 is not running, but the iris 444 is shrunk and the pupil 442 is enlarged. In FIG. 4, the mark 444' stands for the shrunk iris and mark 442' for the enlarged pupil. In contrary, if the time intervals t2-t3' and t4'-t5 are longer than the default time intervals t2-t3 and t4-t5, and the time interval t3'-t4' is shorter than the default time interval t3-t4, it represents that the iris 444 is released and the pupil 442 is shrunk.

Figure 5:
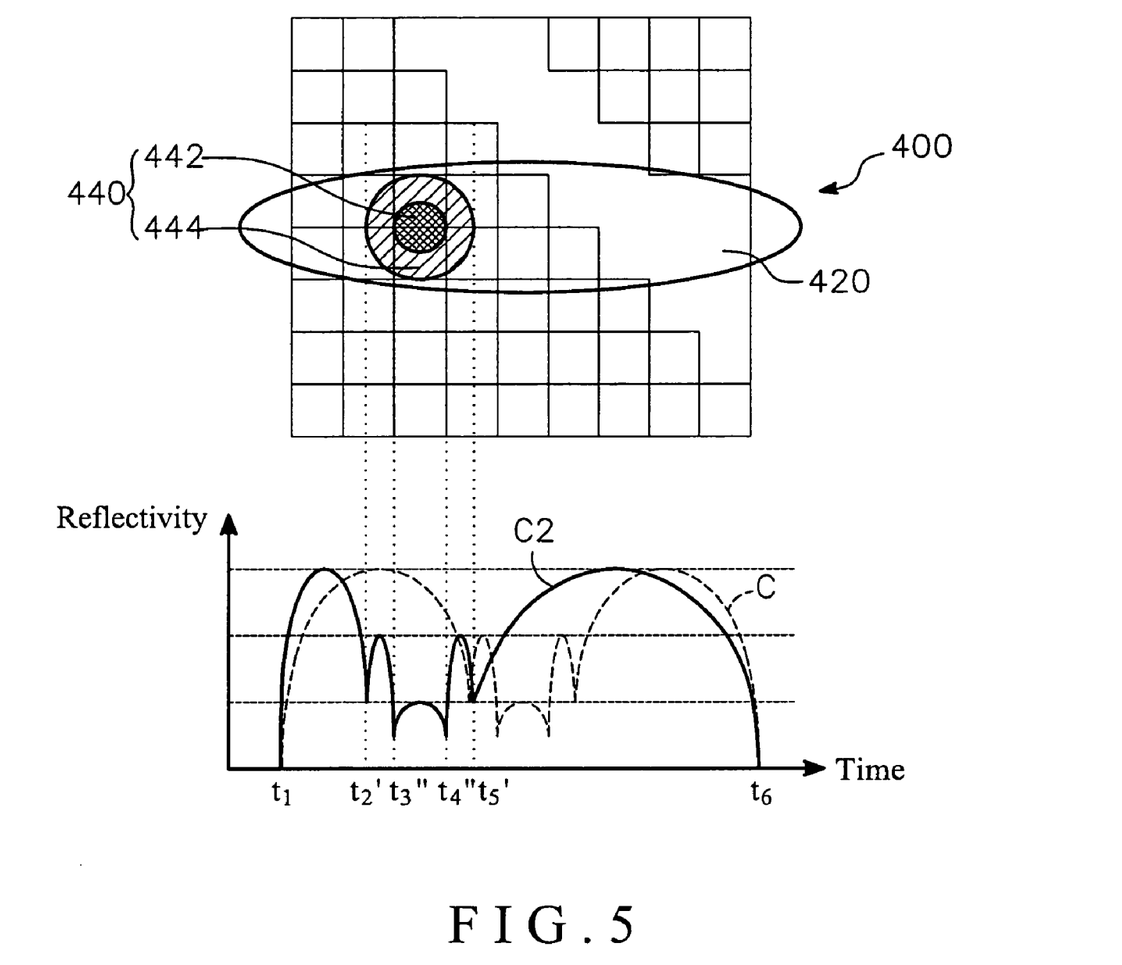

Referring to FIG. 5, comparing the default graph C showing the change of light energy with the graph C2 showing the change of reflected light energy, it appears that when the time interval t1-t2' is shorter than the default t1-t2', but the t5'-t6 is longer than the default t5-t6, it represents that the eyeball 400 is running and the pupil 442 is moving to the left side of the image. In contrary, if the time interval t1-t2' is longer than the default t1-t2', but t5'-t6 is shorter than the default t5-t6, it represents that the pupil 442 is moving to the right side of the image. In addition, if the time intervals t2'-t3", t3"-t4", t4"-t5' are different from the time intervals t2-t3, t3-t4, t4-t5 in the default graph C showing the change of light energy, it represents that the pupil 442 is enlarged or shrunk.

Figure 6:
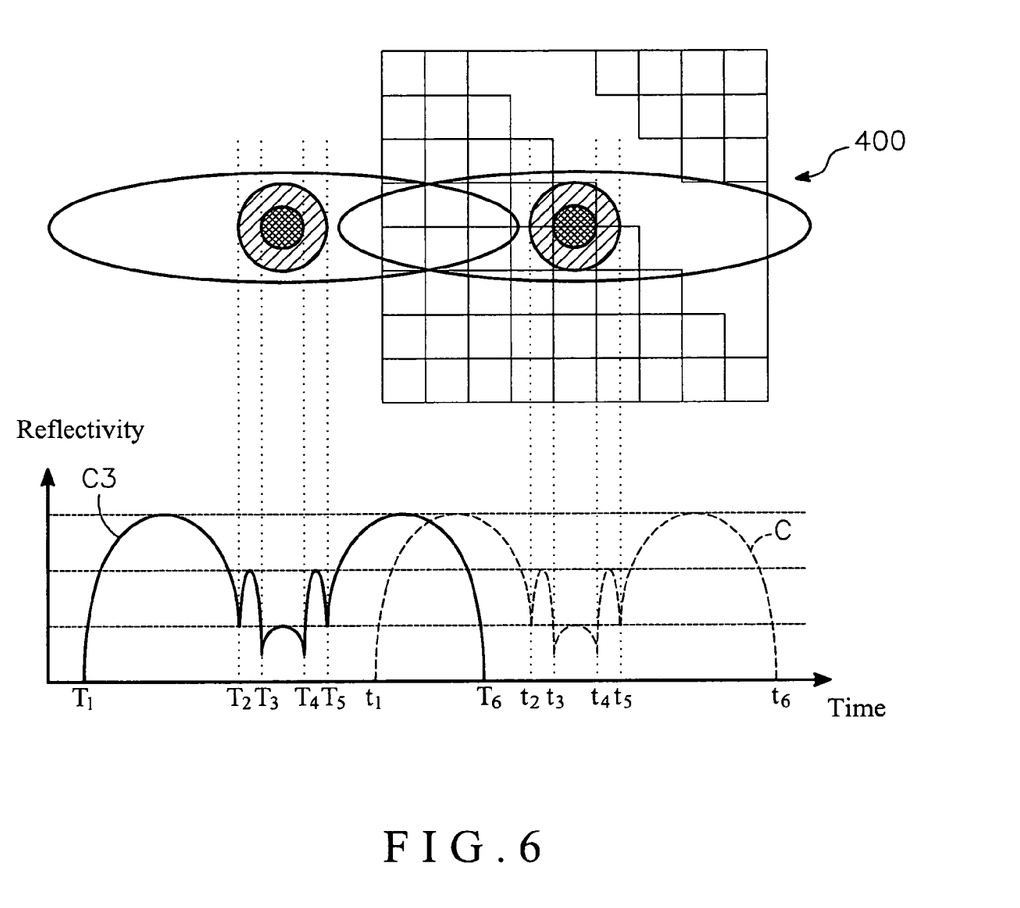

Referring to FIG. 6, the graph C3 showing the change of reflected light energy is the result of the default graph C showing the change of light energy shifting left. Under this circumstance, the time points T1, T2, T3, T4, T5, T6 depart from the default time points t1, t2, t3, t4, t5, t6, which means the eyeball 400 moves left, such as the head turning or moving; the same principle is suitable for judging the eyeball 400 moving right. As shown in FIG. 4 or FIG. 5, each time interval within t1-t6 changes along with the iris 442 changing or the eyeball 400 turning.

Figure 7:
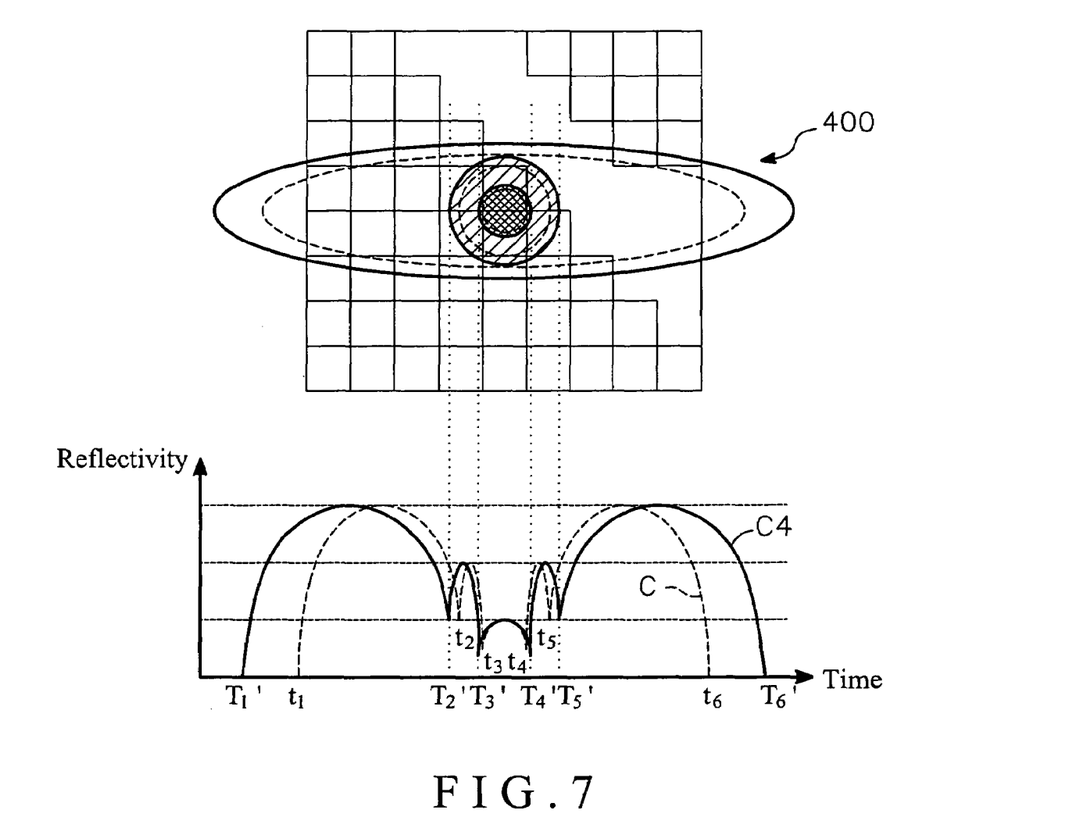

Referring to FIG. 7, the graph C4 showing the change of reflected light energy shows when the default graph C showing the change of light energy is enlarged, the time points T1', T2', T3' shift to the left of the default time points t1, t2, t3, and the time points T4', T5', T6' shift to the right of the default time points t4, t5, t6. It represents the eyeball 400 moves back and forth, such as the face moving back and forth. As shown in FIG. 4 or FIG. 5, each time interval within t1-t6 changes along with the iris 442 changing or the eyeball 400 turning.

It may be speculated according to the above description that the embodiment of the present invention is also suitable for the eyeball 400 running up and down.

According to FIG. 7, the movement of the eyeball 400 running back and forth may be detected, thus the distance change between the eyeball 400 and the first matrix optical sensor 340 or the second matrix optical sensor 360 may be defined and the backlight of the display panel 320 and the font size on the image may be adjusted.

Figure 8:
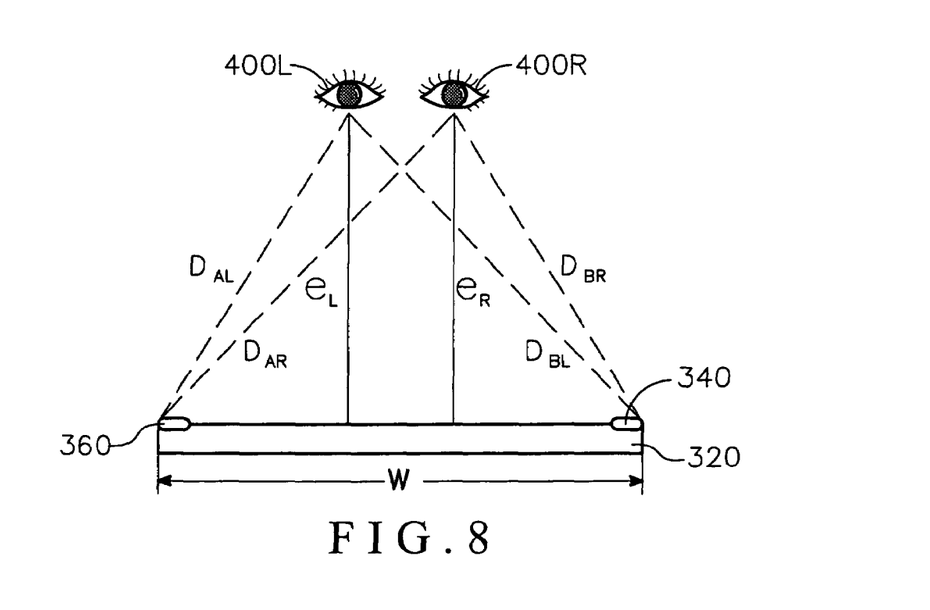
FIG. 8 is a schematic view showing another embodiment of the eyeball locating system according to the present invention.

FIG. 8 provides another method to measure the distance between the eyeball 400 and the first matrix optical sensor 340 or the second matrix optical sensor 360. Referring to FIG. 8, the first matrix optical sensor 340 or the second matrix optical sensor 360 each shines a measuring light on the surface of a left eyeball 400L and a right eyeball 400R, and the light is reflected by the left eyeball 400L and the right eyeball 400R to the first matrix optical sensor 340 or the second matrix optical sensor 360 to form a time difference. According to light speed and the time difference, the distance $D_{BL}$ between the first matrix optical sensor 340 and the left eyeball 400L, the distance $D_{BR}$ between the first matrix optical sensor 340 and the right eyeball 400R, the distance $D_{AL}$ between the second matrix optical sensor 360 and the left eyeball 400L, and the distance $D_{AR}$ between the second matrix optical sensor 360 and the right eyeball 400R are calculated.

In FIG. 8, the distance W between the first matrix optical sensor 340 and the second matrix optical sensor 360 is a known value. The distances $D_{AL}$, $D_{AR}$, $D_{BL}$, $D_{BR}$ between the first matrix optical sensor 340 or the second matrix optical sensor 360 and the left eyeball 400L or the right eyeball 400R are measured by the above method. With these data and trigonometric functions, the vertical distances $e_L$, $e_R$ between the left eyeball 400L, the right eyeball 400R and the display panel 320 may be calculated, thus the backlight of the display panel 320 and the font size on the image are adjusted accordingly.

In addition, in an embodiment, when eyes are closed, it is hard to distinguish the eye white 420 area and the pupil 442 area from the graph showing the change of reflected light energy measured by the first matrix optical sensor 340 and the second matrix optical sensor 360. When eyes are open, the eye white 420 area and the pupil 442 area may be distinguished from the graph showing the change of reflected light energy measured again, thus whether the eyes are blinking and the blinking frequency may also be detected.

The first matrix optical sensor 340 and the second matrix optical sensor 360 may convert the light into electric charge, then into digital signal. In a preferable embodiment, the first matrix optical sensor 340 and the second matrix optical sensor 360 may be, but not limited to a CCD (charge coupled device) sensor, a CMOS (complementary metal-oxide semiconductor) sensor, an infrared sensor, a weak laser sensor or a digital camera module. Its detecting manner is, but not limited to photo, scanning or interlacing type. In addition, single matrix optical sensor is enough to perform the function of the eyeball locating system 300, while multiple matrix optical sensors may improve the accuracy.

The eyeball locating system 300 is used in the electrical device with the display panel 320, such as digital camera, projector, automated teller machine (ATM), media or medical instrument. For example, dispose a matrix optical sensor of the eyeball locating system 300, such as the first matrix optical sensor 340, inside the display panel 320 of the electrical device and set up the application program 380 in its memory (not shown). After the first matrix optical sensor 340 detects the reflecting light from the surface of the eyeball 400, the application program 380 calculates the graph showing the change of reflected light energy and the characteristic value by the microprocessor of the electrical device, so as to handle the electrical device.

The possible application of the embodiment of the present invention is further illustrated as follows: the movement of the eyeball 400 controls the cursor and the blinking defines the shortcut. The blinking speed and number define shortcuts, such as: blinking right eye for confirmation and blinking left eye for cancellation. The intensity of the backlight is adjusted by determining the size of the pupil 442. The change of the pupil 442 is measured by determining the wave, so as to adjust the brightness of the backlight. If no user, the embodiment of the present invention may use to detect the environment, transfer special advertisement and message or even close the computer.

Figure 9:
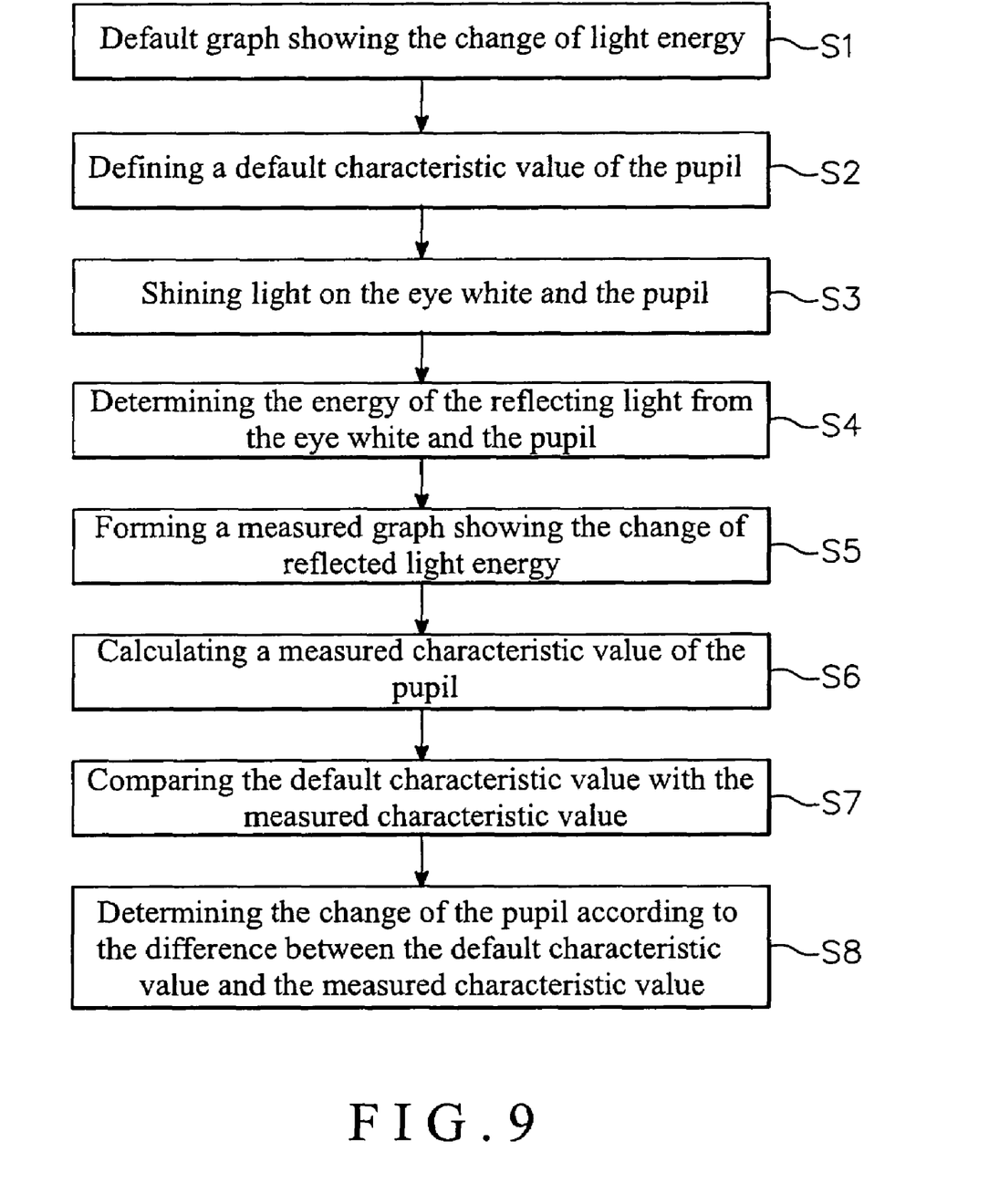
FIG. 9 is a schematic flow chart showing an embodiment of the eyeball locating method according to the present invention.

As shown in FIG. 9, the eyeball locating system 300 has an eyeball locating method, including: providing a default graph C showing the change of light energy (S1); defining a default characteristic value of the pupil 442 according to the default graph C showing the change of light energy (S2); shining light on the eye white 420 and the pupil 442 and making at least a part of the light be reflected by the eye white 420 and the pupil 442, so as to form a reflecting light (S3); detecting the energy of the reflecting light from the eye white 420 and the pupil 442 (S4), so as to form a measured graph C1, C2, C3 or C4 showing the change of reflected light energy (S5); calculating a measured characteristic value of the pupil 442 according to the measured graph C1, C2, C3 or C4 showing the change of reflected light energy (S6); and comparing the default characteristic value with the measured characteristic value (S7) to determine the change of the pupil 442(S8) according to the difference between the default characteristic value and the measured characteristic value.

In an embodiment, the step of comparing the default characteristic value with the measured characteristic value to determine the change of the pupil 442 includes determining the width, displacement or area change of the pupil 442. Furthermore, the step of determining the displacement change of the pupil 442 includes determining the vertical displacement, horizontal displacement and near-far displacement of the pupil 442.

In an embodiment, the time difference between the light traveling from the matrix optical sensor 340 or 360 to the surface of the eyeball 400 and it being reflected to the matrix optical sensor 340 or 360 from the surface of the eyeball 400 is measured. According to the light speed and the time difference, the distance between the matrix optical sensor 340 or 360 and the eyeball 400 is calculated.

The eyeball locating system 300 is used to avoid touching products. Besides closer to the special requirement of general user, it is more suitable for the disabled men and to avoid the bacterial diseases.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An eyeball locating method for measuring the movement of an eyeball comprising an eye white and a pupil, comprising the steps of:

providing a default graph showing a change of light energy of an eyeball;

defining a default characteristic value of the pupil according to the default graph showing the change of light energy;

shining light on the eye white and the pupil wherein at least a part of the light is reflected by the eye white and the pupil, so as to form a reflecting light;

detecting the energy of the reflecting light, so as to form a measured graph showing the change of reflected light energy;

calculating a measured characteristic value according to the measured graph showing the change of reflected light energy; and comparing, using a program stored in a computer-readable medium, the default characteristic value with the measured characteristic value to determine the change of the pupil and to measure the movement of a eyeball.

2. The eyeball locating method of claim 1, wherein the default characteristic value is a default contrast ratio between the eye white and the pupil, and the measured characteristic value is a measured contrast ratio between the eye white and the pupil.

3. The eyeball locating method of claim 1, wherein the default characteristic value is a default width of the pupil, and the measured characteristic value is a measured width of the pupil.

4. The eyeball locating method of claim 1, wherein both the default graph showing the change of light energy and the measured graph showing the change of reflected light energy show the relationship between the light reflectivity and time.

5. The eyeball locating method of claim 1, wherein the step of comparing the default characteristic value with the measured characteristic value to determine the change of the pupil comprises:

determining the width, displacement or area change of the pupil.

6. The eyeball locating method of claim 5, comprising determining the displacement change of the pupil, wherein the step of determining the displacement change of the pupil comprises:

determining a vertical displacement, a horizontal displacement or a near-far displacement of the pupil.

7. The eyeball locating method of claim 1, further comprising the steps of:

providing a matrix optical sensor for shining the light and detecting the energy of the reflected light;

measuring the time difference between the light emitted from the matrix optical sensor and the reflecting light coming back to the matrix optical sensor; and calculating the distance between the matrix optical sensor and the eyeball according to the light speed and the time difference.

8. An eyeball locating apparatus for measuring the movement of an eyeball comprising an eye white and a pupil, comprising:

a display panel;

a matrix optical sensor, disposed in the display panel, for shining light on the eyeball, wherein at least a part of the light is reflected by the eye white and the pupil to form a reflecting light, and detecting the energy of the reflecting light; and an application program, providing a default graph showing the change of light energy of the eyeball to define a default characteristic value of the pupil, and controlling the matrix optical sensor to detect the energy of the reflecting light, so as to form a measured graph showing the change of reflected light energy according to the energy of the reflecting light, wherein the application program calculates a measured characteristic value according to the measured graph showing the change of reflected light energy and compares the default characteristic value with the measured characteristic value to determine the change of the pupil and to measure the movement of a eyeball.

9. The eyeball locating apparatus of claim 8, wherein the matrix optical sensor is disposed at one side of the display panel.

10. The eyeball locating apparatus of claim 8, wherein the matrix optical sensor is selected from the group consisting of a charge-coupled device sensor, a complementary metal-oxide-semiconductor sensor and an infrared sensor.

11. The eyeball locating apparatus of claim 8, wherein the default characteristic value is a contrast ratio between the eye white and the pupil, a width, a displacement, or an area of the pupil.

12. The eyeball locating apparatus of claim 8, wherein the measured characteristic value is a contrast ratio between the eye white and the pupil, a width, a displacement, or an area of the pupil.

13. The eyeball locating apparatus of claim 8, wherein both the default graph showing the change of light energy and the measured graph showing the change of reflected light energy show the relationship between the light reflectivity and time.

14. The eyeball locating apparatus of claim 8, wherein the application program compares the default graph showing the change of light energy with the measured graph showing the change of reflected light energy to determine the distance change between the matrix optical sensor and the eyeball.

15. The eyeball locating apparatus of claim 14, wherein the application program adjusts a backlight of the display panel or a font size on an image shown by the display panel according to the distance change between the matrix optical sensor and the eyeball.

16. The eyeball locating apparatus of claim 8, wherein the application program measures the time difference between the light emitted from the matrix optical sensor and the reflecting light coming back to the matrix optical sensor, and calculates the distance between the matrix optical sensor and the eyeball according to the light speed and the time difference.

17. The eyeball locating apparatus of claim 16, wherein the application program adjusts a backlight of the display panel or a font size on an image shown by the display panel according to the distance change between the matrix optical sensor and the eyeball.

* * * * *